(12) United States Patent
Ratner et al.

(10) Patent No.: US 11,527,327 B2
(45) Date of Patent: Dec. 13, 2022

(54) SYSTEMS AND METHODS FOR DETECTING LIKELIHOOD OF MALIGNANCY FOR A PATIENT USING A PAIR OF MEDICAL IMAGES

(71) Applicant: International Business Machines Corporation, Armonk, NY (US)

(72) Inventors: Vadim Ratner, Haifa (IL); Yoel Shoshan, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 492 days.

(21) Appl. No.: 16/675,309

(22) Filed: Nov. 6, 2019

(65) Prior Publication Data
US 2021/0134460 A1     May 6, 2021

(51) Int. Cl.
| | |
|---|---|
| *G06K 9/00* | (2022.01) |
| *G16H 50/20* | (2018.01) |
| *G16H 30/40* | (2018.01) |
| *G16H 50/50* | (2018.01) |
| *G06T 7/00* | (2017.01) |

(52) U.S. Cl.
CPC .......... *G16H 50/20* (2018.01); *G06T 7/0014* (2013.01); *G06T 7/0016* (2013.01); *G16H 30/40* (2018.01); *G16H 50/50* (2018.01); G06T 2207/20081 (2013.01); G06T 2207/20084 (2013.01);
(Continued)

(58) Field of Classification Search
CPC ........ G16H 50/20; G16H 30/40; G16H 50/50; G16H 20/00; G16H 50/30; G06T 7/0014; G06T 7/0016; G06T 2207/20081; G06T 2207/20084; G06T 2207/30004; G06T 2207/30068
See application file for complete search history.

(56) References Cited

U.S. PATENT DOCUMENTS

| | | | |
|---|---|---|---|
| 2004/0101180 A1* | 5/2004 | Doi | G06T 7/0012 382/128 |
| 2016/0364862 A1* | 12/2016 | Reicher | G06K 9/6227 |

(Continued)

OTHER PUBLICATIONS

Xingwei Wang et al., "Computerized Detection of Breast Tissue Asymmetry Depicted on Bilateral Mammograms: A Preliminary Study of Breast Risk Stratification", Acad Radiol, Oct. 2010, 17(10): 1234-1241.

(Continued)

*Primary Examiner* — Xin Jia
(74) *Attorney, Agent, or Firm* — G. E. Ehrlich

(57) ABSTRACT

There is provided a computer implemented method for detection of likelihood of malignancy in an anatomical image of a patient for planning treatment thereof, comprising: receiving a pair of images that are either of a same patient or from two different patients, wherein the pair of images comprises anatomically corresponding anatomical images each depicting internal anatomical structures of the patient, feeding the pair of images into a model, outputting by the model, an indication of whether the pair of images are of a same patient or not, and generating an indication of likelihood of malignancy when the model wrongly outputs that the pair of images are not of the same patient, when in fact the pair of images are of the same patient, wherein treatment of the patient is planned according to the indication of likelihood of malignancy.

20 Claims, 3 Drawing Sheets

(52) U.S. Cl.
CPC .............. *G06T 2207/30004* (2013.01); *G06T 2207/30068* (2013.01)

(56) References Cited

U.S. PATENT DOCUMENTS

2019/0117146 A1    4/2019  Barbour et al.
2019/0172207 A1*   6/2019  Odry .................... G16H 50/70
2019/0365341 A1*  12/2019  Chan .................... G06N 3/08

OTHER PUBLICATIONS

Daniel Rodrigues Ericeira et al., "Detection of masses based on asymmetric regions of digital bilateral mammograms using spatial description with variogram and cross-variogram functions", Computers in Biology and Medicine, 2013, vol. 43, pp. 987-999.

* cited by examiner

SYSTEMS AND METHODS FOR DETECTING LIKELIHOOD OF MALIGNANCY FOR A PATIENT USING A PAIR OF MEDICAL IMAGES

BACKGROUND

The present invention, in some embodiments thereof, relates to analysis of medical images and, more specifically, but not exclusively, to systems and methods for detection of likelihood of malignancy in a medical image.

Cancer is a leading cause of death. In an effort to catch cancer at an early stage, cancer screening programs are utilized. Certain body parts are imaged, and the images are manually reviewed by a radiologist for visual findings likely representing malignancy. Automated tools are being developed to aid the radiologists in reviewing the large amount of images generated from such screening programs, for example, by identifying certain images as being likely to depict malignancy. The radiologist may manually review the automatically identified images more closely.

SUMMARY

According to a first aspect, a computer implemented method for detection of likelihood of malignancy in an anatomical image of a patient for planning treatment thereof, comprises: receiving a pair of images of a same patient, wherein the pair of images comprises anatomically corresponding anatomical images each depicting internal anatomical structures of the patient, feeding the pair of images into a model, outputting by the model, an indication of whether the pair of images are of a same patient or not, and generating an indication of likelihood of malignancy when the model wrongly outputs that the pair of images are not of the same patient, when in fact the pair of images are of the same patient, wherein treatment of the patient is planned according to the indication of likelihood of malignancy.

According to a second aspect, a computer implemented method for training a model for detection of likelihood of malignancy in an anatomical image of a patient for planning treatment thereof, comprises: providing a set of training images including pairs of anatomically corresponding anatomical images of a plurality of sample patients, wherein each pair of images are either of a same patient or from two different patients, training a model using the training images to identify whether or not a pair of anatomically corresponding anatomical images are of a same target patient, and providing the model, wherein when a target pair of anatomically corresponding anatomical images of a same patient are fed into a model, an indication of malignancy is generated when the model outputs an indication that the pair of images are not of the same patient.

According to a third aspect, a system for detection of likelihood of malignancy in an anatomical image of a patient for planning treatment thereof, comprises: at least one hardware processor executing a code for: receiving a pair of images of a same patient, wherein the pair of images comprises anatomically corresponding anatomical images each depicting internal anatomical structures of the patient, feeding the pair of images into a model, outputting by the model, an indication of whether the pair of images are of a same patient or not, and generating an indication of likelihood of malignancy when the model outputs that the pair of images are not of the same patient, wherein treatment of the patient is planned according to the indication of likelihood of malignancy.

In a further implementation of the first, second, and third aspects, the indication of whether the pair of images are of the same patient is generated when a statistical distance metric between the pair of images is below a threshold, and the indication of likelihood of malignancy denoting that the pair of images are not of the same patient is generated when the statistical distance metric is above the threshold.

In a further implementation of the first, second, and third aspects, the model is implemented based on a Siamese network architecture, wherein each of the pair of images is fed into a respective neural network component that outputs a respective set of features for each anatomical image, and wherein the indication of likelihood of malignancy is generated when a statistical distance between the sets of features of the pair of images is greater than a threshold indicating the pair of images are of the same patient.

In a further implementation of the first, second, and third aspects, the model is trained using training images including only normal images, and excluding malignant images and suspicious images, wherein the training inputs are non-labeled indicative of no malignancy information being provided.

In a further implementation of the first, second, and third aspects, the model is trained using training images of a screening population including low a rate of malignancy below a threshold.

In a further implementation of the first, second, and third aspects, the pair of images are of different symmetric anatomical regions of the patient.

In a further implementation of the first, second, and third aspects, the pair of images are mammographic images of two breasts of the patient.

In a further implementation of the first, second, and third aspects, the pair of images are of a same anatomical region of the patient taken at different times separated by a clinically significant time interval long enough for malignancy to grow.

In a further implementation of the first, second, and third aspects, the pair of images are of a same sensor view.

In a further implementation of the first, second, and third aspects, the model learns a threshold for a statistical distance metric between the pair of anatomically corresponding anatomical images that separates between the pair of images being of the same person and not being of the same person.

In a further implementation of the first, second, and third aspects, the model is implemented based on a Siamese network architecture, wherein each of the pair of images is fed into a respective neural network component that outputs a respective set of features for each anatomical image, and wherein the indication of likelihood of malignancy is generated when a statistical distance between the sets of features of the pair of images is greater than a threshold indicating the pair of images are of the same patient.

In a further implementation of the first, second, and third aspects, the model is trained using training images including only normal images, and excluding malignant images and suspicious images, wherein the training are non-labeled.

In a further implementation of the first, second, and third aspects, the model is trained using training images of a screening population including low a rate of malignancy below a threshold.

In a further implementation of the first, second, and third aspects, the pair of images are of different symmetric anatomical regions of the patient.

In a further implementation of the first, second, and third aspects, the pair of images are mammographic images of two breasts of the patient.

In a further implementation of the first, second, and third aspects, the pair of images are of a same anatomical region of the patient taken at different times separated by a clinically significant time interval long enough for malignancy to grow.

In a further implementation of the first, second, and third aspects, the pair of images are of a same sensor view.

In a further implementation of the third aspect, the at least one hardware processor further executes a code for: providing a set of training images including pairs of anatomically corresponding anatomical images of a plurality of sample patients, wherein each pair of images are either of a same patient or from two different patients, and training the model using the training images to identify whether or not a pair of anatomically corresponding anatomical images are of a same target patient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
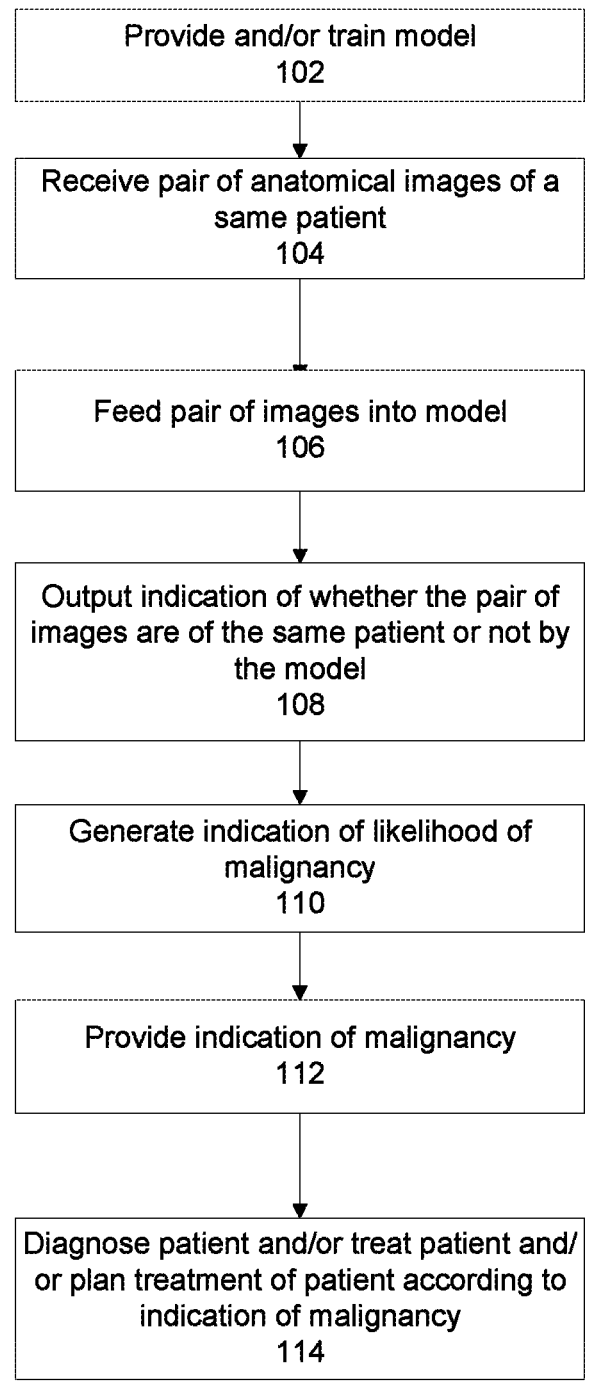
FIG. 1 is a flowchart of a method of detecting likelihood of malignancy for a patient using a pair of anatomical images of the same patient, in accordance with some embodiments of the present invention.

The present invention, in some embodiments thereof, relates to analysis of medical images and, more specifically, but not exclusively, to systems and methods for detection of likelihood of malignancy in a medical image.

As used herein, the term malignancy may sometimes be interchanged with the term anomaly, for example, the systems, methods, apparatus, and/or code instructions described herein may be designed to identify anomalies between the corresponding anatomical images which are not necessarily malignant, but may represent other disease processes, which may be benign and/or non-malignant but require treatment, for example, visual findings indicative of osteoporosis in knees, edema present in one lung but not the other, and changes in thickness of heart muscle in an image taken later in time in comparison to an earlier image.

An aspect of some embodiments of the present invention relates to systems, methods, an apparatus, and/or code instructions (i.e., stored on a memory and executable by one or more hardware processors) for detecting likelihood of malignancy for a patient using a pair of anatomical images of the same patient. The pair of images are anatomically corresponding images each depicting internal anatomical structures of the patient, for example, images captured by an x-ray, CT, MRI, ultrasound, mammography device, and/or nuclear medicine device, as opposed to images depicting the exterior skin surface of the patient such as captured by a visual light sensor, for example, external facial features of the patient. The pair of anatomically corresponding images may each depict a respective symmetrical body part, optionally captured at similar viewing angles, for example, mammography images depicting left and right breasts, CT images depicting a left and right lung, and MRI images depicting a left and right knee joint. Alternatively or additionally, the pair of anatomically corresponding images may each depict the same respective body part, optionally captured at similar viewing angles, where the images are separated by a time interval sufficiency long for visual findings to develop, for example, CT images depicting a liver separated by one year to check for metastases in the liver, ultrasound images of a heart separated by three years to check for thickening of heart muscle, and mammographic images of a left breast separated by two years to check for breast cancer. The pair of images are fed into a model, which outputs an indication of whether the pair of images are of a same patient or not. An indication of likelihood of malignancy is generated when the model wrongly outputs that the pair of images are not of the same patient. Since the pair of images are actually of the same patient, but the model wrongly identifies the images as being of two different patients, one of the two images includes an abnormality likely to be malignancy. The abnormality present in one of the images caused the two images to appear to the model as originating from two different people. The patient may be diagnosed according to the indication, and/or treatment of the patient may be planned according to the indication, for example, additional imaging of the patient may be performed, a biopsy may be performed, surgery may be performed, chemotherapy may be administered, radiation therapy may be administered, and/or a watch and wait approach may be selected.

An aspect of some embodiments of the present invention relates to systems, methods, an apparatus, and/or code instructions (e.g., stored in a memory and/or data storage device and executable by one or more hardware processors) for training a model for detecting likelihood of malignancy for a patient using a pair of anatomical images of the same patient. A set of training inputs, consisting of pairs of anatomically corresponding anatomical images either from the same patient or from different patients for multiple sample patients, is provided. Optionally, all of the images of the training dataset depict normal and/or non-malignancy findings. Optionally, none of the images of the training dataset depict malignant and/or other target visual findings. Alternatively, the rate of images depicting a malignancy in one of the images but not the other is relatively low, for example, statistically similar to the rate in a screening population. The model is trained using the training set to identify whether or not a pair of anatomically corresponding anatomical images are of a same target patient. The model is provided to process a new target pair of anatomically corresponding anatomical images of a same patient. An indication of malignancy is generated when the model outputs an indication that the pair of images are not of the same patient (when the pair actually is of the same patient).

At least some implementations of the systems, methods, apparatus, and/or code instructions described herein improve the technology of automated medical image analysis for detection of anomalies, for example, likelihood of cancer. Standard approaches used by radiologists are based on a manual comparison of anatomically corresponding pairs of images, for example, images of corresponding anatomical regions of corresponding anatomical parts, such as left and right symmetrical body parts, captured using corresponding optionally similar sensor viewing angles, and/or pairs of images of the same body part separated by time captured using corresponding optionally similar sensor viewing angles, such as a current chest x-ray and another chest x-ray taken a year prior to the current x-ray. When the two regions look similar, the radiologist assumes that the tissues are normal. When the two regions look different to the radiologist, the radiologist may more closely scrutinize the respective regions on the assumption that the difference is based on an anomaly which may require further investigation, for example, to diagnose cancer or exclude cancer (or other medical problems). However, manually checking for asymmetry in symmetrical body parts is difficult, since body parts not considered asymmetric by a human radiologist may still contain a significant amount of difference. Moreover, manually checking for medically significant findings based on differences between the two images of the same body part separated by a time interval is a difficult task, since the body may have naturally changed over time with non-malignant changes, such as due to aging and/or non-relevant medical processes.

The technical challenge lies in that two symmetrical body parts are still different, since they are two different body parts and may vary in anatomical detail depicted by respective images. Moreover, the two images of the same body part may represent the same body part at different states of life and as such may vary anatomically. The technical challenge is determining when the difference between the two symmetrical body parts (and/or the same body part) is normal, and when the difference between the two symmetrical body parts (and/or the same body part) depicts an abnormality such as likelihood of malignancy. At least some implementations of the systems, methods, apparatus, and/or code instructions described herein address the technical challenge by the model that learns the threshold that separates between two symmetrical body parts that are different but normal, and two symmetrical body parts where one (or both) of the body parts are different due to an abnormality such as likelihood of malignancy. Alternatively or additionally, the model learns the threshold that separates between the same two body parts that are different due to non-malignancy effects occurring over time (and/or due to effects occurring at the time of image capture), and the same two body parts that are different due to malignancy (or other clinically important changes). The pair of images are fed to the trained model, and the model is conceptually asked "Is it the same patient"? Since the difference between the symmetrical body parts (and/or the same body part over time) in a healthy and/or normal patient is smaller (i.e., below the threshold) than for a sick patient, asymmetry (and/or time difference) indicative of abnormality (e.g., likelihood of cancer) is detected.

At least some implementations of the systems, methods, apparatus, and/or code instructions described herein improve medical treatment of patients, by improving the ability to select patients for further investigation of anomalies in tissues, which may be cancerous. The automated analysis of pairs of images of the same patient may improve the accuracy of selecting patients for further investigation of possibly anomalies over other automated methods and/or over manual methods.

At least some implementations of the systems, methods, apparatus, and/or code instructions described herein address the technical problem of asymmetry detection. Standard approaches for training machine learning models are based on supervised learning using labeled data, for example, images labeled by a radiologist as depicting malignancy and/or other diagnostic information after manual review. At least some implementations of the systems, methods, apparatus, and/or code instructions described herein are based on unsupervised learning using unlabelled data for training the model. The use of unlabelled images enables the expected output of the model (i.e., the decision whether or not the input images are from the same patient) to be derived automatically, without any need for a radiologist (i.e., no need to manually analyze medical records and/or images).

At least some implementations of the systems, methods, apparatus, and/or code instructions described herein are based on detecting anomaly by exclusion. A model may be trained to identify whether or not two images are of the same person. When two new images of the same person are received by the model, but classified by the model as not being of the same person, the incorrect classification is indicative of an anomaly in one of the images. The correct classification by the model as being of the same person is indicative of the images depicting normal (i.e., non-anomalous) tissue.

At least some implementations of the systems, methods, apparatus, and/or code instructions described herein are different than other standard approaches for analysis of medical images by asymmetrical detection. For example:

Some other approaches are based on comparing patterns of hemoglobin transition in different areas. The pattern comparison is based on detecting differences of hemoglobin signatures. In contrast, at least some implementations of the systems, methods, apparatus, and/or code instructions described herein are based on a model that learns a distance function between the two anatomical regions, and detects an anomaly when the distance is greater than a threshold, as described herein.

Other approaches are based on supervised labeling of images. The labeling may be automatically performed using graphical and/or clinical reports to derive the training labels. In contrast, at least some implementations of the systems, methods, apparatus, and/or code instructions described herein are based on non-supervised approaches without training labels.

Yet another method relates to detecting body part asymmetry by registration to detect corresponding regions of the two sides, and then comparing the regions using a support vector machine. In contrast, at least some implementations of the systems, methods, apparatus, and/or code instructions described herein learn a distance (i.e., symmetry) function between two sides using unlabeled data, and detect an anomaly when the distance is greater than a threshold, as described herein.

In yet another approach, body part asymmetry is determined by comparing the values of 20 pre-determined heuristic features (that may or may not accurately represent the information contained within an image). In contrast, at least some implementations of the systems, methods, apparatus, and/or code instructions described herein train a model directly from the images themselves.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
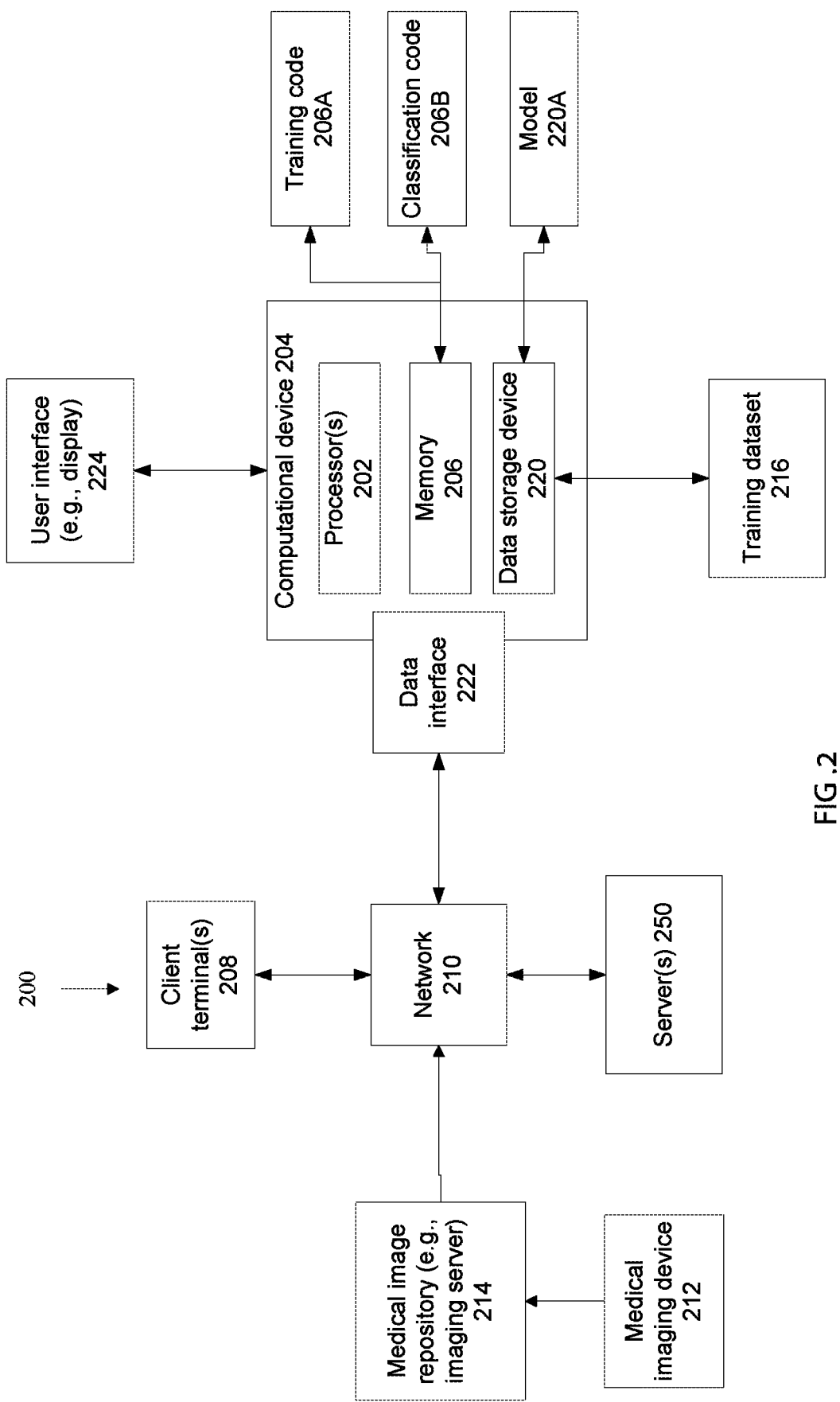
FIG. 2 is a block diagram of components of a system for detecting likelihood of malignancy for a patient using a pair of anatomical images of the same patient, in accordance with some embodiments of the present invention.
Figure 3:
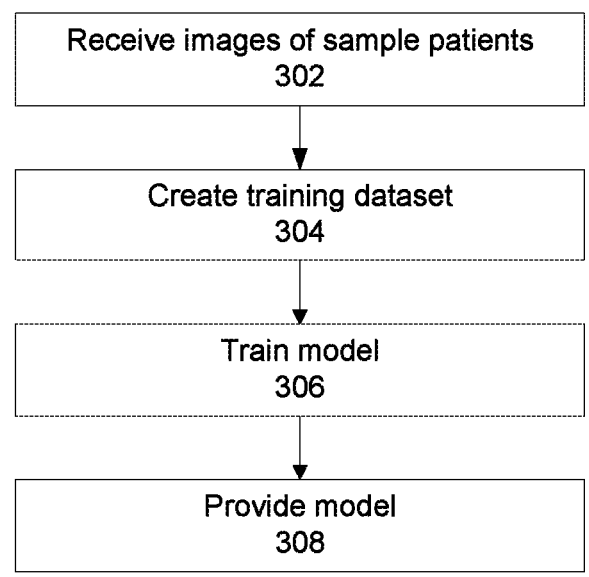
FIG. 3 is a flowchart of a method of training a model for detecting likelihood of malignancy for a patient using a pair of anatomical images of the same patient, in accordance with some embodiments of the present invention.

Reference is now made to FIG. 1, which is a flowchart of a method of detecting likelihood of malignancy for a patient using a pair of anatomical images of the same patient, in accordance with some embodiments of the present invention. Reference is also made to FIG. 2, which is a block diagram of components of a system 200 for detecting likelihood of malignancy for a patient using a pair of anatomical images of the same patient, in accordance with some embodiments of the present invention. Reference is now made to FIG. 3, which is a flowchart of a method of training a model for detecting likelihood of malignancy for a patient using a pair of anatomical images of the same patient, in accordance with some embodiments of the present invention. System 200 may implement the features of the method described with reference to FIG. 1 and/or FIG. 3, by one or more hardware processors 202 of a computing device 204 executing code instructions stored in a memory (also referred to as a program store and/or storage device) 206, for example, training code 206A, classification code 206B, and/or model code 220A.

Computing device 204 may be implemented as, for example one or more and/or combination of: a client terminal, a server, a radiology workstation, an imaging server (e.g., PACS), an electronic medical record (EMR) server, a virtual machine, a virtual server, a computing cloud, a mobile device, a desktop computer, a thin client, a smartphone, a tablet computer, a laptop computer, a wearable computer, glasses computer, and a watch computer.

Computing device 204 may be implanted as an add-on to clinical software, for example, to a radiology workstation, a PACS server (or other medical imaging storage server), an EMR server, and/or other patient management software.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., client terminal used by a user for viewing medical images, client terminal running EMR access software, client terminal running patient management software, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application and/or EMR viewing application and/or other patient management application, and/or providing functions using a remote access session to the client terminals 208, such as through a web browser, application programming interface (API), and/or software development kit (SDK).

Computing device 204 receives pairs of medical images, each pair including at least one medical image from each symmetrical body part of the same individual and/or including two images from the same body part separated by a significantly long time interval, by an imaging device(s) 212, for example, two dimensional images, three dimensional images, a sequence of 2D medical images, and/or a three dimensional (3D) medical imaging device from which 2D images are optionally extracted as slices (e.g., CT, tomosynthesis, MRI). Medical imaging machine(s) 212 may include a mammogram machine, a CT scanner, an MRI machine, a tomosynthesis device, and an ultrasound machine.

Pair of medical images captured by imaging machine 212 may be stored in an imaging repository 214, for example, an imaging storage server, a data storage server, a computing cloud, a PACS server (picture archiving and communication system), and a hard disk. The medical images stored by medical image repository 214 include pairs of medical images of patients for analysis, and/or pairs of medical images of sample patients included in a training dataset 216 for training the model, as described herein.

Computing device 204 may receive the medical image(s) via one or more data interfaces 222, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may store classification code 206B that execute one or more acts of the method described with reference to FIG. 1 and/or training code 206A that execute one or more acts of the method described with reference to FIG. 3.

Computing device 204 may include a data storage device 220 for storing data, for example, a trained model 220A as described herein, and/or training dataset 216 as described herein. Data storage device 220 may be implemented as, for example, a memory, a local hard-drive, a removable storage unit, an optical disk, a storage device, a virtual memory and/or as a remote server and/or computing cloud (e.g., accessed over network 210). It is noted that model 220A may be stored in data storage device 220, for example, with executing portions loaded into memory 206 for execution by processor(s) 202.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208 and/or server(s) 250, for example, when computing device 204 acts as a server providing services (e.g., SaaS) to remote radiology terminals, PACS servers, EMR servers, medical servers and/or other remove devices, by analyzing remotely obtained medical images as described herein.

Server(s) 250, for example, to obtain updates to model 220A.

Medical image repository (e.g., imaging server) 214, for example, to obtain the pair(s) of medical image(s) of the patient for analysis, and/or to obtain medical image(s) of sample patients for inclusion in the training dataset for training the model.

Computing device 204 includes and/or is in communication with a user interface(s) 224 that includes a mechanism designed for a user to enter data (e.g., select patient medical images for analysis) and/or view the analysis. Exemplary user interfaces 224 include, for example, one or more of, a touchscreen, a display, a keyboard, a mouse, and voice activated software using speakers and microphone.

Referring now back to FIG. 1, at 102, a model for detecting likelihood of malignancy for a patient using a pair of anatomical images of the same patient is provided and/or trained, for example, as described with reference to FIG. 3.

Optionally, the model includes a classifier component and an output component. The classifier component of the model may identify whether or not a pair of anatomically corresponding anatomical images are of a same target patient. The likelihood of malignancy may be generated by the output component when the classifier component of the model determines that the pair of images are not of the same patient (i.e., when the pair of images actually do depict the same patient). Alternatively, the model includes the classifier component, with the output component being a separate component that receives the output of the classifier component. As used herein, the term model may sometimes refer to the classifier component alone, and may sometimes refer to the combination of the classifier component and the output component.

Optionally, the classifier component of the model is implemented based on a Siamese network architecture, for example, as described with reference to Chopra, S., Hadsell, R. and LeCun, Y., 2005, June. *Learning a similarity metric discriminatively, with application to face verification*. In CVPR (1) (pp. 539-546), incorporated herein by reference in its entirety.

Different models may be provided, for example, per property of corresponding anatomical images (i.e., images of different symmetrical body parts, such as left and right breast, and left lung and right lung, or images of the same body part separated by a significant amount of time such as liver images separated by 6 months), and/or per type of anatomical imaging modality (e.g., CT, x-ray, MRI, nuclear medicine scan, mammography, PET, ultrasound), and/or per target tissue and/or per target cancer type (e.g., breast and/or breast cancer, prostate and/or prostate cancer, colon and/or colon cancer, esophagus and/or esophageal cancer, liver and/or liver cancer, pancreas and/or pancreatic cancer, brain and/or brain cancer, lung and/or lung cancer).

At 104, a pair of anatomical images of a same patient is received.

The pair of images are anatomically corresponding images, where each image depicts internal anatomical structures of the patient, for example, images captured by an x-ray, CT, MRI, ultrasound, mammography device, and/or nuclear medicine device. Anatomical images are different than images depicting the exterior skin surface of the patient, for example, the face of the patient, such as captured by a visual light sensor or other sensors that capture images at wavelengths that do not significantly penetrate tissue below the surface of the skin.

Optionally, the pair of anatomically corresponding images each depict a respective symmetrical body part, for example, a right body part and a corresponding left body part. For example, mammography images depicting left and right breasts, CT images depicting a left and right lung, and MRI images depicting a left and right knee. For example, in the case of mammographic images, the following represent exemplary pairs of images: left cranial-caudal view (LCC) and right cranial-caudal view (RCC), and another pair is left mediolateral oblique view (LMLO) and right mediolateral oblique view (RMLO).

Alternatively or additionally, the pair of anatomically corresponding images may each depict the same body part, where the images are separated by a time interval sufficiency long for visual findings to develop, for example, CT images depicting a liver separated by one year to check for metastases in the liver, ultrasound images of a heart separated by three years to check for thickening of heart muscle, and mammographic images of a left breast separated by two years to check for breast cancer.

Optionally, the pair of anatomically corresponding images and/or the pair of images separated by time, are captured at a same sensor view (i.e., statistically similar, within a range of tolerance), for example, a pair of chest x-rays captured at an AP view (anterior-posterior), and a pair of mammographic images captured using LCC and RCC views, and a pair of mammographic images captured using LMLO and RMLO views.

The pair of anatomical images may be received, for example, from a PACS server, from a data storage device, from a client terminal, from a removable storage device (e.g., CD ROM, disc on key, USB connected device).

The pair of anatomical images may be 2D images. The 2D images may be directly captured by the imaging modality device, for example, 2D x-rays and/or 2D ultrasound images. The 2D image may be extracted from a 3D imaging dataset, for example, 2D slices, for example, from a CT scan, an MRI scan, and/or a nuclear medicine scan.

At 106, the pair of images are fed into the model.

When the model is implemented based on the Siamese network architecture, each of the pair of images is fed into a respective neural network component of the model that outputs a respective set of features for each anatomical image.

Optionally, a feature extraction sub-network (e.g., the first part of the network) has shared weights and processes both fed image inputs in the same logic. The output of each sub-network may be a one dimensional feature vector.

During training, the parameters of the feature extraction sub-networks may change so that (e.g., usually) the cosine distance between the first and second image inputs is minimal and/or small (e.g., below a threshold) when the two images depict the same body portion of the same person (i.e., symmetrical body part portions, and/or the same body portion at different times), and/or the cosine distance is maximal and/or large (e.g., above the threshold, where the threshold for small and large may be the same threshold or respective different thresholds) when the two images depict body portions of different people, which represents significant differences between the body portion of the same person that appear as if the two body portions are of different people (when in fact they are of the same person, denoting likelihood of malignancy).

At 108, an indication of whether the pair of images are of a same patient or not is outputted by the model.

When the model is implemented based on the Siamese network architecture, the indication of likelihood of malignancy is generated when a statistical distance between the sets of features of the pair of images (outputted by respective neural network components) is greater than a threshold indicating the pair of images are of the same patient. The threshold level may be set, for example, manually based on user input, as a predefined system value, and/or automatically computed.

The indication may be a binary indication, for example, whether the pair of images are for the same person or not, or a single classification label, for example, output only when the pair of images are for the same person, or only output when the pair of images are not for the same person.

Alternatively or additionally, the output of the model includes a probability of accuracy of whether the pair of images are for the same patient or not.

At 110, an indication of likelihood of malignancy is generated when the model outputs that the pair of images are not of the same patient.

Optionally, the indication of whether the pair of images are of the same patient is generated when a statistical distance metric between the pair of images is below the threshold (or above the threshold), and the indication of likelihood of malignancy denoting that the pair of images are not of the same patient is generated when the statistical distance metric is above the threshold (or below the threshold).

At 112, the indication of likelihood of malignancy is provided, for example, presented on a display, stored as metadata associated with the medical image(s) (e.g., in the PACS server), and/or stored in a field in the electronic health record of the patient, and/or forwarded to another storage device and/or server.

At 114, the patient may be diagnosed according to the indication and/or treatment of the patient is planned according to the indication and/or the patient may be treated according to the indication. For example, additional imaging of the patient may be performed, a biopsy may be performed, surgery may be performed, chemotherapy may be administered, radiation therapy may be administered, and/or a watch and wait approach may be selected.

Referring now back to FIG. 3, at 302, anatomical images for multiple sample patients is received, for example, from the PACS server, from the anatomical imaging device, and/or from another storage device.

At 304, a set of training images is created.

Optionally, the training images are not labeled (i.e., no malignancy information is associated with (e.g., attached to) an image), which may represent a form of self-supervised and/or semi-supervised learning.

The input image pairs are either from the same patient or from different patients.

The set of training images is created by pairing anatomically corresponding images for each patient or for different patients, according to the desired target output of the model. Images of symmetrical body parts may be paired (e.g., a respective mammographic image of a left and a right breast optionally at the same sensor viewing angle), and/or images of the same body part separated by a time interval may be paired.

Optionally, only images depicting normal findings are selected for the training set. Images depicting non-normal and/or malignant and/or suspicious findings may be excluded. Alternatively, only images depicting non-malignant findings are selected for the training dataset, for example, images depicting normal findings and/or images depicting suspicious findings. Images depicting malignant findings may be excluded.

Alternatively, the images are obtained for a screening population, having a low rate of malignancy, for example, below a defined threshold. For example, images obtained as part of a cancer screening program are obtained. The rate of cancer found in the images may be expected to be similar to a cancer rate of a general population of patients targeted for screening.

Excluding malignant images from the training set and/or having a set of images with low malignancy rates, for which the two images of the pair are expected to look very similar to one another, may improve accuracy of the model in detecting when one of the images is not similar to the other, i.e., generating the indication that the pair of images are not for the same patient.

The creation of the training dataset may be performed manually (e.g., by a user) and/or automatically by code, since patient, body part and viewpoint of an image are automatically stored in most electronic health record systems, and as such are readily available.

At 306, the model (i.e., the classifier component) is trained using the training images.

The model is trained to identify whether or not a pair of anatomically corresponding anatomical images are of a same target patient or not.

The model learns a threshold for a statistical distance metric between the pair of anatomically corresponding anatomical images that separates between the pair of images being of the same person and not being of the same person.

Utilizing the significantly larger amount of available images depicting normal and/or healthy patients, and the anatomical variations between different patients, the neural network component of the model learns the distance metric between corresponding anatomical body portions. The distance metric represent a learned symmetric metric and/or a learned similarity metric, which is learned by the neural network without explicitly defining the metric, to differentiate between symmetrical body portions and/or between the same body portion at different times, to detect likelihood of malignancy.

The model may be implemented based on a Siamese network architecture. Each of the pair of images is fed into a respective neural network component that outputs a respective set of features for each anatomical image. The indication of likelihood of malignancy is generated when a statistical distance between the sets of features of the pair of images is greater than a threshold indicating the pair of images are of the same patient.

At 308, the model is provided, for example, stored in a data storage device and/or transmitted to another computing device.

The classifier component and the output component may be provided. Alternatively, the classifier component is provided, and an existing output component is used.

In response to feeding target pairs of anatomically corresponding anatomical images of a same patient (e.g., into the classifier component), an indication of malignancy is generated (e.g., by the output component) when the model (e.g., classifier component) outputs an indication that the pair of images are not of the same patient.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images will be developed and the scope of the term anatomical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for detection of likelihood of malignancy in an anatomical image of a patient for planning treatment thereof, comprising:
    determining a likelihood of malignancy when a model fed by a pair of images of a same patient wrongly identifies the pair of images as not belonging to the same patient, when in fact the pair of images are of the same patient, by:
        receiving the pair of images of the same patient, wherein the pair of images comprises anatomically corresponding anatomical images each depicting internal anatomical structures of the patient;
        feeding the pair of images into the model,
        outputting by the model, an indication of whether the pair of images are of the same patient or not; and
        generating an indication of likelihood of malignancy when the model wrongly outputs that the pair of images are not of the same patient, wherein treatment of the patient is planned according to the indication of likelihood of malignancy.

2. The computer implemented method of claim 1, wherein the indication of whether the pair of images are of the same patient is generated when a statistical distance metric between the pair of images is below a threshold, and the indication of likelihood of malignancy denoting that the pair of images are not of the same patient is generated when the statistical distance metric is above the threshold.

3. The computer implemented method of claim 1, wherein the model is implemented based on a Siamese network architecture, wherein each of the pair of images is fed into a respective neural network component that outputs a respective set of features for each anatomical image, and wherein the indication of likelihood of malignancy is generated when a statistical distance between the sets of features of the pair of images is greater than a threshold indicating the pair of images are of the same patient.

4. The computer implemented method of claim 1, wherein the model is trained using training images including only normal images, and excluding malignant images and suspicious images, wherein the training inputs are non-labeled indicative of no malignancy information being provided.

5. The computer implemented method of claim 1, wherein the model is trained using training images of a screening population including low a rate of malignancy below a threshold.

6. The computer implemented method of claim 1, wherein the pair of images are of different symmetric anatomical regions of the patient.

7. The computer implemented method of claim 1, wherein the pair of images are mammographic images of two breasts of the patient.

8. The computer implemented method of claim 1, wherein the pair of images are of a same anatomical region of the patient taken at different times separated by a clinically significant time interval long enough for malignancy to grow.

9. The computer implemented method of claim 1, wherein the pair of images are of a same sensor view.

10. A computer implemented method for training a model for detection of likelihood of malignancy in an anatomical image of a patient for planning treatment thereof, comprising:
  providing a set of training images including pairs of anatomically corresponding anatomical images of a plurality of sample patients, wherein each pair of images are either of a same patient or from two different patients;
  training a model using the training images to identify whether or not a pair of anatomically corresponding anatomical images are of a same target patient; and
  providing the model, wherein when a target pair of anatomically corresponding anatomical images of a same patient are fed into a model, an indication of malignancy is generated when the model outputs an indication that the pair of images are not of the same patient.

11. The computer implemented method of claim 10, wherein the model learns a threshold for a statistical distance metric between the pair of anatomically corresponding anatomical images that separates between the pair of images being of the same person and not being of the same person.

12. The computer implemented method of claim 10, wherein the model is implemented based on a Siamese network architecture, wherein each of the pair of images is fed into a respective neural network component that outputs a respective set of features for each anatomical image, and wherein the indication of likelihood of malignancy is generated when a statistical distance between the sets of features of the pair of images is greater than a threshold indicating the pair of images are of the same patient.

13. The computer implemented method of claim 10, wherein the model is trained using training images including only normal images, and excluding malignant images and suspicious images, wherein the training are non-labeled.

14. The computer implemented method of claim 10, wherein the model is trained using training images of a screening population including low a rate of malignancy below a threshold.

15. The computer implemented method of claim 10, wherein the pair of images are of different symmetric anatomical regions of the patient.

16. The computer implemented method of claim 10, wherein the pair of images are mammographic images of two breasts of the patient.

17. The computer implemented method of claim 10, wherein the pair of images are of a same anatomical region of the patient taken at different times separated by a clinically significant time interval long enough for malignancy to grow.

18. The computer implemented method of claim 10, wherein the pair of images are of a same sensor view.

19. A system for detection of likelihood of malignancy in an anatomical image of a patient for planning treatment thereof, comprising:
  at least one hardware processor executing a code for:
    determining a likelihood of malignancy when a model fed by a pair of images of a same patient wrongly identifies the pair of images as not belonging to the same patient, when in fact the pair of images are of the same patient, by:
      receiving the pair of images of the same patient, wherein the pair of images comprises anatomically corresponding anatomical images each depicting internal anatomical structures of the patient;
      feeding the pair of images into the model,
      outputting by the model, an indication of whether the pair of images are of same patient or not; and
      generating an indication of likelihood of malignancy when the model wrongly outputs that the pair of images are not of the same patient, wherein treatment of the patient is planned according to the indication of likelihood of malignancy.

20. The system of claim 19, wherein the at least one hardware processor further executes a code for:
  providing a set of training images including pairs of anatomically corresponding anatomical images of a plurality of sample patients, wherein each pair of images are either of a same patient or from two different patients; and
  training the model using the training images to identify whether or not a pair of anatomically corresponding anatomical images are of a same target patient.

* * * * *